United States Patent
Monden et al.

(10) Patent No.: US 6,191,192 B1
(45) Date of Patent: *Feb. 20, 2001

(54) ANTIBACTERIAL POLYMERIC MOLDINGS

(75) Inventors: Noriko Monden; Masahiro Seko; Hideyuki Yokota; Masakazu Tanaka; Susumu Arimori, all of Otsu (JP)

(73) Assignee: Toyo Boseki Kabushiki Kaisha, Osaka (JP)

(*) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/100,250

(22) Filed: Jun. 19, 1998

(30) Foreign Application Priority Data

| Jun. 23, 1997 | (JP) | 9-165978 |
| Aug. 6, 1997 | (JP) | 9-211790 |
| Jan. 29, 1998 | (JP) | 10-016765 |
| Feb. 2, 1998 | (JP) | 10-021051 |
| Apr. 8, 1998 | (JP) | 10-096002 |
| Apr. 27, 1998 | (JP) | 10-116831 |

(51) Int. Cl.[7] ............................. A61M 25/00
(52) U.S. Cl. ........................... 523/122; 604/265
(58) Field of Search ............... 523/122; 604/265

(56) References Cited

U.S. PATENT DOCUMENTS

| 3,325,436 | * | 6/1967 | Prindle et al. | 523/122 |
| 4,392,848 | * | 7/1983 | Lucas | 604/265 |
| 4,479,795 | * | 10/1984 | Mustacich et al. | 604/265 |
| 4,539,234 | * | 9/1985 | Sakamoto et al. | 604/265 |
| 4,581,028 | * | 4/1986 | Fox et al. | 604/265 |
| 4,675,347 | * | 6/1987 | Mochizuki et al. | 523/122 |
| 4,847,088 | * | 7/1989 | Blank | 424/78 |
| 4,902,503 | * | 2/1990 | Unemura et al. | 604/265 |
| 5,089,205 | * | 2/1992 | Huang et al. | 264/305 |
| 5,741,526 | * | 4/1998 | Miyata | 424/635 |

FOREIGN PATENT DOCUMENTS

| 0 516 184 | 11/1988 | (EP) . |
| 1-136663 | 5/1989 | (JP) . |
| 2-24544 | 5/1990 | (JP) . |
| 3-6822 | 1/1991 | (JP) . |
| 3-10341 | 2/1991 | (JP) . |
| 3-27213 | 4/1991 | (JP) . |
| 3-64143 | 10/1991 | (JP) . |
| 4-502111 | 4/1992 | (JP) . |
| 4-74026 | 11/1992 | (JP) . |
| 5-123392 | 5/1993 | (JP) . |
| 5-80225 | 11/1993 | (JP) . |
| 5-88900 | 12/1993 | (JP) . |
| 6-11813 | 2/1994 | (JP) . |
| 6-56902 | 3/1994 | (JP) . |
| 6-34817 | 5/1994 | (JP) . |
| 6-55892 | 7/1994 | (JP) . |
| 84/01721 | 5/1984 | (WO) . |
| 90/01956 | 3/1990 | (WO) . |

* cited by examiner

*Primary Examiner*—Veronica P. Hoke
(74) *Attorney, Agent, or Firm*—Foley & Lardner

(57) ABSTRACT

The invention provides an antibacterial polymeric molded product containing an anionic compound capable of combining, by ionic bond, with a cationic component of a water-soluble antibacterial agent, wherein the cationic component is combined with the anionic compound by ionic bond at least at the surface of the molded product.

8 Claims, No Drawings

ANTIBACTERIAL POLYMERIC MOLDINGS

FIELD OF THE INVENTION

The present invention relates to antibacterial polymeric moldings and more particularly to antibacterial polymeric molded products suitable as urethral catheters, gloves or the like, and to a process for preparing the molded product.

PRIOR ART

The urethral catheter is a medical device designed to stay in an organism, and therefore, has been disinfected or sterilized by some means before use. However, the urethral catheter is mostly used for a long time, thus frequently failing to remain aseptic during use. The urethral catheter can not be kept aseptic because of penetration of bacteria from outside via the inside or outside of the catheter passageway which is responsible for the development of infectious diseases such as urethritis, cystitis, pyelonephritis or the like. Consequently there is now a demand for improvements in urethral catheters.

As a preventive measure against infectious diseases, chemotherapy has been performed by the administration of antibiotics or the like. However, the chemotherapy requires the administration of antibiotics in large doses, unavoidably entailing a problem of side effects depending on the type of antibiotics. While chemotherapy can temporarily sterilize the bacteria, the patient, once seized with such diseases, would be likely to become reinfected upon advent of resistant bacteria. Hence this problem would be attendant on chemotherapy not deliberately conducted.

The most effective measure against infectious diseases is to impart an antibacterial property to the urethral catheter in its entirety or the surface thereof.

Typical examples of antibacterial agents are heavy metals such as gold, silver, copper and zinc and their metal compounds. These antibbacterial agents have a broad antibacterial spectrum as metal ions against bacteria and fungi even in extremely small amounts. Attempts have been heretofore made to produce urethral catheters with their matrix containing these metal compounds to make the catheters antibacterial.

Quaternary ammonium salts are cationic antibacterial substances and available as other antibacterial compounds than the metal compounds. The quaternary ammonium salts show a high antibacterial activity and have been incorporated, like the metal compounds, into the matrix of urethral catheters to make the catheters antibacterial.

Further, a need has arisen for antibacterial gloves as well as for antibacterial urethral catheters, such as gloves for medical use in operations or inspection or for food-processing purposes in order to prevent the contagion of infectious diseases or to improve the hygienic conditions.

A composition comprising a natural rubber latex or a synthetic rubber latex containing silver protein (Japanese Examined Patent Publication No.88900/1993) and a composition comprising silicone rubber containing silver protein (Japanese Examined Patent Publication No.55892/1994) are reported as antibacterial compositions comprising a polymeric compound containing a silver-based antibacterial substance. The application of a silver-based antibacterial substance in urethral catheters is reported in Japanese Examined Patent Publication No.34817/1994 which discloses a coating composition comprising a natural rubber latex or a synthetic rubber latex containing silver protein used in a process for producing a urethral catheter by a coating method such as a dipping method.

Japanese Examined Patent Publication No.11813/1994 discloses an antibacterial composition comprising a natural rubber latex containing a cationic antibacterial substance. Japanese Examined Patent Publication No.74026/1992 discloses a urethral catheter produced from silicone rubber having a water-soluble cationic antibacterial substance dispersed therein as urethral catheters containing a cationic antibacterial substance. Further, Japanese Examined Patent Publication No.64143/1991 describes a urethral catheter produced from an organic high molecular elastomer having a sparingly water-soluble quaternary ammonium salt dispersed therein.

However, various drawbacks are entailed in molding processes using the above-mentioned compositions comprising an organic high molecular compound having dispersed therein an antibacterial substance such as silver protein or quaternary ammonium salt. For example, it is difficult in the process to maintain the antibacterial substance as stably dispersed in the organic high molecular compound for a long time. Further, the latex particles are likely to aggregate and the antibacterial substance (especially metal compounds) tends to precipitate, resulting in formation of ununiform coating layer and difficulty in obtaining a stable antibacterial property.

Other problems are posed by processes using an organic high molecular compound having an antibacterial substance dispersed therein. For example, after molding the desired product from the organic high molecular compound, the molded product is exposed to a high temperature in post treatment such as vulcanization so that the antibacterial substance is oxidized or thermally decomposed, tending to lower the stability owing to the decomposition product and to form, in some case, black particles due to the precipitation of silver or like antibacterial component.

The antibacterial substance can be introduced into a urethral catheter or the like otherwise than by dispersing the antibacterial substance in the base material. For example, Japanese Examined Patent Publication No.10341/1991 discloses a method wherein a solution containing a biguanide compound as a water-soluble antibacterial substance is absorbed into the urethral catheter, and then the antibacterial substance is converted into a sparingly water-soluble compound. Also available is a method wherein after molding a latex, the molded product is immersed before cure into a solution containing an antibacterial substance to absorb the antibacterial substance into the molded product, as disclosed in Japanese Unexamined Patent Publication (PCT) No.502111/1992.

However, the above-mentioned methods of introducing the antibacterial substance into a urethral catheter using a solution containing the antibacterial substance are not economical because the antibacterial substance is slowly absorbed into the base material and the operation takes several days. Further, the antibacterial substance dissolves out early during use so that the antibacterial activity may be retained only for a short period.

Also known is a producing method wherein a coating layer having maleic anhydride group is formed on the surface of the urethral catheter using a composition containing a polyfunctional compound and a copolymer containing maleic anhydride as a monomer component and then the antibacterial substance is bonded to the coating layer after hydrolysis of maleic anhydride group, as disclosed in Japanese Examined Patent Publication No.24544/1990. However, this method requires the step of forming a coating layer containing maleic anhydride group and the step of hydrolyzing the maleic anhydride group, that is, posing a problem of involving an increased number of steps.

DISCLOSURE OF THE INVENTION

A primary object of the present invention is to provide an antibacterial polymeric molded product having a high antibacterial property and an ability to sustain a high antibacterial activity for a long time.

Another object of the invention is to provide an antibacterial molded product which is suitable as an antibacterial urethral catheter or as antibacterial gloves.

A further object of the invention is to provide a process capable of easily producing an antibacterial organic polymeric molded product which can sustain a high antibacterial activity for a long time.

The present inventors conducted extensive research to achieve the foregoing objects and found that the contemplated molded product can be produced by the following processes. Proposed is a process wherein the molded product is produced from a polymeric compound containing an anionic compound capable of combining, by ionic bond, with a cationic component of a water-soluble antibacterial agent (which anionic compound may be hereinafter referred to simply as an "anionic compound") and then the molded product is brought into contact with an aqueous solution of containing a water-soluble antibacterial agent. Another process is proposed wherein the molded product is produced from a polymeric compound, and then is caused to absorb the anionic compound, followed by contacting the anionic compound-containing molded product with an aqueous solution containing a water-soluble antibacterial agent.

According to these proposed processes, the cationic component of the water-soluble antibacterial agent is combined with the anionic compound in the molded product to form a sparingly water-soluble antibacterial compound which exists at least at the surface of the molded product. Consequently the obtained molded product can maintain a high antibacterial property for a long time.

The present invention was completed based on this novel finding.

According to the present invention, there are provided the following antibacterial polymeric molded products and the following processes for preparing them.

1. An antibacterial polymeric molded product containing an anionic compound capable of combining, by ionic bond, with a cationic component of a water-soluble antibacterial agent, wherein the cationic component is combined with the anionic compound by ionic bond at least at the surface of the molded product.

2. The molded product as defined in item 1, wherein the molded product containing the anionic compound is one molded from a polymeric compound containing the anionic compound.

3. The molded product as defined in item 1, wherein the moleded product containing the anionic compound is one produced by contacting a polymeric molded product with an aqueous solution containing the anionic compound to cause the molded product to absorb the anionic compound.

4. The molded product as defined in any one of items 1 to 3, which is one formed from natural rubber, synthetic rubber, silicone rubber or a synthetic polymeric compound.

5. The molded product as defined in any one of items 1 to 3, wherein the water-soluble antibacterial agent is at least one member selected from the group consisting of silver compounds, quaternary ammonium salts and quaternary phosphonium salts.

6. The molded product as defined in any one of items 1 to 3, wherein the anionic compound is a compound containing in the molecule at least one anionic group selected from carboxyl groups and sulfonic acid groups.

7. The molded product as defined in item 6, wherein the anionic compound is at least one compound selected from the group consisting of amino acid derivatives, long-chain carboxylic acids, salts of long-chain carboxylic acids, sulfonic acids and salts of sulfonic acids.

8. The molded product as defined in item 1 which is an antibacterial urethral catheter.

9. The molded product as defined in item 1 which is an antibacterial glove.

10. A process for preparing the molded product of any one of items 1, 2 and 4–9, the process comprising the steps of molding a polymeric compound containing an anionic compound capable of combining, by ionic bond, with a cationic component of a water-soluble antibacterial agent; and contacting the molded product with an aqueous solution containing an water-soluble antibacterial agent.

11. A process for preparing the molded product of any one of items 1 and 3–9, the process comprising the steps of molding a polymeric compound; contacting the molded product with an aqueous solution containing an anionic compound capable of combining, by ionic bond, with a cationic component of a water-soluble antibacterial agent; and contacting the molded product with an aqueous solution containing a water-soluble antibacterial agent.

Described below are the components which are used for preparing the antibacterial polymeric molded product of the present invention.

Polymeric Compound

In preparing the antibacterial polymeric molded product of the present invention, natural rubber, silicone rubber, synthetic rubber, a synthetic polymeric compound or like organic polymeric compound can be used as the polymeric compound, i.e. the base material for the molded product.

Of these materials, natural rubber is inexpensive and is excellent in mechanical properties. In preparing the molded product from natural rubber for medical use such as urethral catheters or gloves, it is important to use a latex thoroughly purified for removing an allergenic substance and to leach the molded product to a satisfactory degree. Careful consideration should be taken to check the safety of compounds to be added for vulcanization.

For example, an allergenic reaction due to protein can be prevented when using a deproteinized natural rubber latex, i.e. a natural rubber latex highly purified to remove the dissolved protein, as disclosed in Japanese Unexamined Patent Publication No.56902/1994.

Silicone rubber has been used long in medical applications because of its high safety as a medical material and superior biocompatibility. Thus, silicone rubber is suitable as a base material for urethral catheters or gloves for medical use. Examples of the silicone rubber to be used in the invention are dimethyl polysiloxane, methylphenyl polysiloxane, methylvinyl polysiloxane, fluoroalkylmethyl polysiloxane and the like.

Examples of the synthetic rubber useful in the invention are homopolymers or copolymers of vinyl monomers such as ethylene, styrene, vinyl acetate, vinyl chloride, vinylidene chloride, acrylonitrile or the like, homopolymers or copolymers of diene monomers such as butadiene, isoprene, chloroprene, 1,3-pentadiene, 1,5-hexadiene or the like, and copolymers of said vinyl monomers and diene monomers.

Other synthetic polymeric compounds useful in the invention are, for example, polyether urethane, polyurethane, polyurethane urea, polyvinyl chloride, polyester, polypropylene, polyethylene, ethylene-vinyl alcohol copolymers, vinyl acetate-vinyl alcohol copolymers and so on. Among them, preferred are polyvinyl chloride, polyurethane, polyether urethane, ethylene-vinyl alcohol copolymers, vinyl acetate-vinyl alcohol copolymers and the like.

Water-Soluble Antibacterial Agent

The water-soluble antibacterial agent for use in the invention can be any of antibacterial agents which can form a cationic component having an antibacterial property when dissolved in water. Examples of such antibacterial agents are silver compounds, quaternary ammonium salts, quaternary phosphonium salts and the like.

Preferred silver compounds are silver nitrate, silver acetate, silver perchlorate and the like which have a high solubility in water, a low molecular weight and a high reactivity.

Quaternary ammonium salts and quaternary phosphonium salts useful in the invention include, for example, compounds represented by the formula

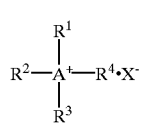

(I)

wherein $R^1$, $R^2$ and $R^3$ are the same or different, and each represents alkyl group having 1 to 12 carbon atoms, aryl group having 6 to 12 carbon atoms or aralkyl group having 7 to 20 carbon atoms, R is alkyl group having 1 to 25 carbon atoms, A is nitrogen atom or phosphorus atom and X is chlorine atom or bromine atom.

The alkyl group having 1 to 12 carbon atoms and represented by $R^1$, $R^2$ and $R^3$ in the compound of the formula (I) includes linear or branched chain alkyl groups, preferably alkyl groups having 1 to 8 carbon atoms. Specific examples of such alkyl groups are methyl, ethyl, propyl, isopropyl, butyl, tert-butyl, pentyl, hexyl and the like. Preferred aryl groups having 6 to 12 carbon atoms are substituted or unsubstituted phenyl or naphthyl groups such as phenyl, tolyl, xylyl and the like which may have 1 to 3 substituents such as methyl, ethyl, butyl, methoxy, ethoxy and the like. Among them, preferred are aryl groups having 6 to 10 carbon atoms. Examples of the aralkyl group having 7 to 20 carbon atoms are benzyl, phenethyl, phenylbutyl, diphenylmethyl, triphenylmethyl, naphthylmethyl, naphthylethyl and the like. The alkyl group having 1 to 25 carbon atoms and represented by $R^4$ in the formula (I) is linear or branched chain alkyl group. Examples include lauryl, myristyl, cetyl and stearyl as well as the above examples. Among them, preferred are alkyl groups having 3 to 20 carbon atoms and more preferred are those having 6 to 20 carbon atoms.

Examples of the quaternary ammonium moiety in the quaternary ammonium salt of the formula (I) are tributyl lauryl ammonium, tributyl myristyl ammonium, tributyl cetyl ammonium, tributyl stearyl ammonium, triphenyl lauryl ammonium, triphenyl myristyl ammonium, triphenyl cetyl ammonium, triphenyl stearyl ammonium, benzyldimethyl lauryl ammonium, benzyldimethyl myristyl ammonium, benzyldimethyl cetyl ammonium, benzyldimethyl stearyl ammonium and the like. Examples of the quaternary phosphonium moiety in the quaternary phosphonium salt are tributyl lauryl phosphonium, tributyl myristyl phosphonium, tributyl cetyl phosphonium, tributyl stearyl phosphonium, triphenyl lauryl phosphonium, triphenyl myristyl phosphonium, triphenyl cetyl phosphonium, triphenyl stearyl phosphonium, benzyldimethyl lauryl phosphonium, benzyldimethyl myristyl phosphonium, benzyldimethyl cetyl phosphonium, benzyldimethyl stearyl phosphonium and the like.

In the present invention, the above-mentioned water-soluble antibacterial agents such as silver compounds, quaternary ammonium salts, quaternary phosphonium salts and the like can be used either alone or in combination.

Anionic Compound

A compound containing in the molecule at least one anionic group selected from carboxyl groups and sulfonic acid groups is preferable as the anionic compound capable of combining with a cationic component of a water-soluble antibacterial agent by ionic bond. At least one anionic group in one molecule suffices. Preferred examples of the anionic compound are compounds (i) to (iii) given below.

(i) Amino Acid Derivative

It is preferred to use N-acyloyl amino acid or its salts represented by the formula (II) as the amino acid derivative:

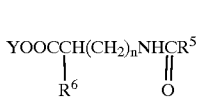

(II)

wherein $R^5$ is alkyl group having 6 to 20 carbon atoms, $R^6$ is hydrocarbon group having 1 to 10 carbon atoms which group may contain at least one of nitrogen, sulfur and oxygen atoms, or hydrogen atom, Y is H or Na, and n is an integer of 0 to 6. Examples of the group $R^5$ include those exemplified above as the alkly group of 6 to 20 carbon atoms among the examples of the group $R^4$. Examples of the group $R^6$ include:

—H, —CH$_3$, —CH(CH$_3$)$_2$, —CH$_2$CH(CH$_3$)$_2$, —CH(CH$_3$)CH$_2$CH$_3$, —CH$_2$C$_6$H$_5$, —CH$_2$C$_8$H$_5$NH, —CH$_2$CH$_2$SCH$_3$, —CH$_2$OH, —CH(OH)CH$_3$, —CH$_2$SH, —CH$_2$C$_6$H$_4$OH, —CH$_2$CONH$_2$, —CH$_2$CH$_2$CONH$_2$, —CH$_2$COOH, —CH$_2$CH$_2$COOH, —(CH$_2$)$_4$NH$_2$ and —(CH$_2$)$_3$NHC(=NH)NH$_2$.

Specific examples of the amino acid derivative represented by the formula (II) are sodium N-lauroyl-L-glutamate, sodium N-myristoyl-L-glutamate, sodium N-cetoyl-L-glutamate, sodium N-stearoyl-L-glutamate and the like.

These amino acid derivatives can be used either alone or in combination.

(ii) Long-Chain Carboxylic Acid and Salt Thereof

Preferred examples of long-chain carboxylic acids are saturated or unsaturated carboxylic acids containing at least one carboxyl group and having 10 to 40 carbon atoms. Examples of their salts are alkali metal salts such as sodium salt, potassium salt and the like. Specific examples of long-chain carboxylic acids and their salts are stearic acid, sodium stearate, lauric acid, sodium laurate and the like.

These long-chain carboxylic acids and their salts can be used either alone or in combination.

(iii) Sulfonic Acid and Salt Thereof

Useful sulfonic acids include those containing at least one sulfonic acid group such as saturated or unsaturated aliphatic sulfonic acids having 1 to 40 carbon atoms, aromatic sulfonic acids and the like. Examples of their salts are alkali metal salts such as sodium salt, potassium salt and the like.

Aliphatic sulfonic acids and salts thereof may contain at least one amino group. Examples are dodecylsulfonic acid, taurine, salts thereof and the like.

Aromatic sulfonic acids and salts thereof are, for example, alkylbenzenesulfonic acid containing alkyl group of 6 to 20 carbon atoms such as dodecylbenzenesulfonic acid, alkali metal salts thereof, sulfanilic acid, alkali metal salts thereof, and compounds represented by the formula (III)

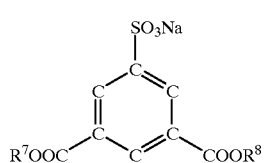

(III)

wherein $R^7$ and $R^8$ are the same or different and each represents alkyl group having 1 to 12 carbon atoms or a group represented by —$C_nH_{2n}OH$ (wherein n is an integer of 1 to 12).

Examples of the alkyl group having 1 to 12 carbon atoms in the formula (III) include the above-mentioned examples of the alkyl group in the formula (I).

Among the compounds of the formula (III), the salts of sulfonic acids with their safety assured for organisms are sodium salt of dimethyl-5-sulfoisophthalate, sodium salt of diethyl-5-sulfoisophthalate, sodium salt of dibutyl-5-sulfoisophthalate, sodium salt of dihexyl-5-sulfoisophthalate, sodium salt of dioctyl-5-sulfoisophthalate, sodium salt of di(6-hydroxyhexamethylene)-5-sulfoisophthalate, sodium salt of di(6-hydroxyoctamethylene)-5-sulfoisophthalate and the like.

These sulfonic acids and their salts can be used either alone or in combination.

The above-mentioned anionic compounds (i) to (iii) can be used singly or in combination with the same or different species among the compounds (i) to (iii).

Process for Preparing the Antibacterial Polymeric Molded Product

The antibacterial polymeric molded product according to the present invention can be prepared, for example, by the following two processes.

(1) A first process for preparing the antibacterial polymeric molded product comprises the steps of molding a polymeric compound containing an anionic compound, and bringing the molded product into contact with an aqueous solution containing a water-soluble antibacterial agent.

According to the first process, the anionic compound is incorporated into a polymeric compound as the base material for the contemplated molded product.

When natural rubber or synthetic rubber is used as the base material, the anionic compound may be dispersed into a natural rubber latex or a synthetic rubber latex. In incorporating the anionic compound into the latex, the anionic compound may be directly mixed with the latex, or the anionic compound may be dispersed well with a dispersing agent by a ball mill and then may be mixed with the latex.

The latex to be usually used is one having about 40 to about 60% solids content.

A natural rubber latex having the anionic compound dispersed therein has a pH of preferably at least 5, more preferably at least 7 and most preferably 7–12 in view of dispersibility.

When silicone rubber or other synthetic polymeric substance is used as the base material, the anionic compound may be uniformly mixed with other components before the molding operation.

A suitable amount of the anionic compound to be used is about 0.001 to about 10 parts by weight, preferably about 0.01 to about 5 parts by weight, per 100 parts by weight of the solids of polymeric compound as the base material. When the anionic compound is used in the above amount, a proper amount of the antibacterial component can be bound to the base material having the properties not substantially impaired.

The polymeric compound may further contain curing agents, additives and the like conventionally used to the same degree as heretofore intended, according to the type of the polymeric compound. For example, when a natural rubber latex or a synthetic rubber latex is vulcanized, a sulfur compound, zinc white, vulcanization accelerator, aging inhibitor and the like may be added to the base material.

Then, an article is molded in the desired shape from the polymeric compound having the anionic compound dispersed therein.

An article is molded in the conventional manner according to the type of polymeric compound used.

For example, when a natural rubber latex or a synthetic rubber latex is used as the base material, an article is molded by a dipping method. Stated more specifically, a dipping mold applied with a coagulant is immersed in a latex solution, and the mold is withdrawn to coagulate the latex. Then, this operation is repeated until a coating layer of required thickness is formed.

When silicone rubber is used as the base material, the base material may be molded by the conventional method. For example, the desired tubular product can be obtained by an extrusion method.

When a synthetic polymeric compound is used as the base material, the base material may be molded by the conventional method. For example, when polyurethane is used, the desired product can be obtained by a melt extrusion method.

After molding, the molded product is brought into contact with an aqueous solution containing a water-soluble antibacterial agent. This treatment may be conducted at any optional stage after molding. For example, it may be done after or before heat-curing the molded product or after completion of molding operation.

The aqueous solution containing a water-soluble antibacterial agent may be one adjusted to a concentration of antibacterial agent in the range of about 0.0001 to about 5% by weight, preferably about 0.001 to about 0.5% by weight. A sufficient amount of antibacterial component can be bound to the molded product insofar as the concentration of antibacterial agent is in the above-specified range.

There is no limitation on the method of contacting the molded product with the aqueous solution containing a water-soluble antibacterial agent. The mode of immersing the molded product in the aqueous solution is favorable because the mode can be easily carried out and it can bind a satisfactory amount of antibacterial component to the molded product.

The conditions for immersing the molded product in the aqueous solution are not limited insofar as they are within the range which does not adversely affect the polymeric compound as the base material and the antibacterial agent. Usually the solution temperature is about 20 to about 150° C., preferably about 30 to about 100° C. The immersion period is variable depending on the solution temperature and is usually about 5 minutes to about one week, preferably about 10 minutes to about 3 days. It is preferred to shake the molded product as immersed in the aqueous solution.

The molded product is usually cured by heat treatment. The heat treatment is carried out in the conventional manner according to the type of polymeric compound used. Suitable heat treatment conditions are selected from the ranges of about 50 to about 200° C. and about 10 minutes to about 2 weeks. The heat treatment may be done either before or after treatment with the aqueous solution containing a water-soluble antibacterial agent. When the heat treatment is conducted after treatment with the aqueous solution, preferably mild conditions are employed to prevent the antibacterial component from change of properties. Preferred conditions are selected from the ranges of about 50 to about 150° C. and about 10 minutes to about 24 hours.

When required, other conventional treatments may be carried out according to the type of polymeric compound used as the base material. For example, when a natural rubber latex or a synthetic rubber latex is used, usually leaching may be conducted after molding and chlorination may be performed after curing using, e.g. an aqueous solution containing a mixture of sodium hypochlorite and hydrochloric acid.

In the molded product thus obtained, the cationic component of a water-soluble antibacterial agent is combined with the anionic compound in the molded product to form a sparingly water-soluble compound containing the cationic component of antibacterial agent.

(2) A second process for preparing the antibacterial polymeric molded product according to the invention comprises the steps of molding a polymeric compound, contacting the molded product with an aqueous solution containing an anionic compound and contacting the molded product with an aqueous solution containing a water-soluble antibacterial agent.

According to the second process, first the polymeric compound used as the base material is molded into the desired shape. In the second process, the polymeric compound is molded in the same manner as in the first process described above in (1) except that the polymeric compound does not contain the anionic compound.

Subsequently the molded product is contacted with an aqueous solution containing the anionic compound, whereby the anionic compound is absorbed into the molded product.

The contact of the molded product with an aqueous solution containing the anionic compound may be carried out at the desired stage after molding, namely either before or after heat treatment.

Although variable with the solubility of the anionic compound, the concentration of the anionic compound in the aqueous solution is preferably about 0.0001 to about 30% by weight, more preferably about 0.001 to about 10% by weight.

While the method of contacting the molded product with the aqueous solution is not limited, the mode of immersing the molded product in the aqueous solution is favorable because the operation is easy and a sufficient amount of the anionic compound can be absorbed.

The conditions for immersion are not limited insofar as they are within the range which does not adversely affect the polymeric compound used as the base material. The solution temperature is preferably about 25 to about 120° C., more preferably about 30 to about 100° C. The immersion period is preferably about 1 minute to about 48 hours, more preferably about 5 minutes to about 24 hours, although variable with the solution temperature.

After the anionic compound is absorbed into the molded product in this way, the molded product is contacted with an aqueous solution containing a water-soluble antibacterial agent. This operation may be effected at the desired stage after contact of the molded product with the aqueous solution containing the anionic compound. For example, the operation may be performed continuously after contact with the aqueous solution containing the anionic compound. Optionally, for example, the anionic compound is absorbed into the molded product before heat treatment, then, heat treatment is practiced and the molded product may be contacted with the aqueous solution containing a water-soluble antibacterial agent.

The contact with the aqueous solution containing a water-soluble antibacterial agent can be conducted in the same manner as described above in item (1).

Other conditions for preparing the molded product may be the same as described above in item (1).

In the molded product thus obtained, the anionic compound absorbed into the molded product binds with the cationic component of water-soluble antibacterial agent, thereby forming a sparingly water-soluble compound containing the cationic component.

Antibacterial Polymeric Molded Product

According to the above-mentioned two processes, the anionic compound is incorporated into the polymeric compound before molding, or the anionic compound is absorbed, after molding, into the molded product, whereby the molded product containing the anionic compound is obtained. And then the anionic compound in the molded product combinds, by ionic bond, with the cationic component of the water-soluble antibacterial agent, giving a sparingly water-soluble compound containing the cationic component. The sparingly water-soluble compound exists at least at the surface of the molded product. Depending on the treatment conditions, the cationic component of antibacterial agent permeates into the molded product to form, inside the molded product, a sparingly water-soluble compound containing the cationic component of antibacterial agent.

Of the above-mentioned two processes, the second process is advantageous in the following. The second process comprises causing the molded product to absorb the anionic compound and contacting the molded product with the aqueous solution containing a water-soluble antibacterial agent. In the second process, the anionic compound is not incorporated into the polymeric compound when the polymeric compound is molded. Thus, when molding an article by a dipping method from a natural rubber latex or a synthetic rubber latex, the anionic compound does not react with the coagulant deposited on the dipping mold and effectively acts, on contact with the aqueous solution containing an antibacterial agent, to easily bind a sufficient amount of antibacterial component to the molded product.

When the antibacterial polymeric molded product is produced by the above-mentioned two processes, the antibacterial substance need not be uniformly dispersed in the polymeric compound used as the base material, and the antibacterial component can be imparted to the molded product under mild conditions by the immersion of molded product into the aqueous solution. In short, the operation is easily carried out. Further, when the antibacterial component is bonded after heat-treating the molded product, the thermal decomposition of antibacterial substance can be prevented. Moreover, the antibacterial component can be chemically bonded with high efficiency mainly to the surface of molded product which requires the antibacterial property. This eliminates a need for extra amount of antibacterial component. Hence the process is economical.

In the molded product according to the invention, the antibacterial agent is soluble in water before binding to the anionic compound, but is made sparingly soluble in water due to the reduction of solubility in water after binding to the anionic compound. Consequently the antibacterial component is unlikely to flow out or dissolve out during the use of molded product so that a high antibacterial property is shown during the service life of the molded product. Moreover, because of the antibacterial substance existing on the surface of molded product, a high antibacterial activity is shown immediately after use.

According to the invention, the antibacterial component is bonded to the molded product by ionic bond after molding. Consequently a molded product with the predefined contour can be easily produced without dimensional change which would occur as when the molded product is coated with a composition containing an antibacterial component.

The antibacterial molded products according to the invention can be effectively used, for example, as antibacterial gloves for medical use or for food-processing purposes, antibacterial urethral catheters such as Foley catheter, balloon catheter, Trocar catheter, Nélaton catheter and bladder catheter or the like.

EXAMPLES

The present invention is described below in more detail with reference to the following examples wherein the parts or percentages are all by weight.

Example 1

A natural rubber latex specimen was prepared by adding 0.3 part of zinc dimethyldithiocarbamate, 1.5 parts of sulfur colloid, 3.0 parts of activated zinc and 0.5 part of sodium dimethyl-5-sulfoisophthalate to 100 parts of a natural rubber latex having a solids concentration of 60%. The natural rubber latex specimen had a pH of 10.0.

A dipping mold for molding a urethral catheter was immersed in the obtained natural rubber latex specimen and was withdrawn from the latex specimen. The molded product thus obtained was dried at 80° C. for 10 minutes. This operation was repeated until a molded product of 1.6 mm thickness was obtained. Finally the molded product was dried at 70° C. for 12 hours. Then the molded product was washed in flowing water for one week and was dried, giving a urethral catheter. The obtained urethral catheter was immersed in an aqueous solution of silver nitrate adjusted to a concentration of 0.05% and was shaken at 30° C. for 12 hours. Thereafter the urethral catheter was washed with water and was dried at 70° C., giving an antibacterial urethral catheter.

The obtained urethral catheter was cut to a length of 5 cm and was sterilized with ethylene oxide gas. A suspension of *Pseudomonas aeruginosa* in an amount of $1 \times 10^5$ cells/ml was prepared using a broth solution diluted 50-fold with a physiological saline. The urethral catheter was immersed into the suspension and shaking culture was conducted at 37° C. for 24 hours. The number of cells in the suspension after cultivation was counted by a smear method to evaluate the antibacterial property. The same evaluation was also made using *Escherichia coli* and *Staphylococcus aureus*. The results are shown in Table 1.

Example 2

A natural rubber latex specimen was prepared by adding 0.5 part of zinc salt of 2-mercaptobenzothiazole, 1.5 parts of sulfur colloid, 1.0 part of activated zinc and 0.1 part of taurine to 100 parts of a natural rubber latex having a solids concentration of 60%. The natural rubber latex specimen had a pH of 10.0. A dipping mold for molding a urethral catheter was immersed in the obtained natural rubber latex specimen and was withdrawn from the latex specimen. The molded product thus obtained was dried at 80° C. for 10 minutes. This operation was repeated until a molded product of 1.6 mm thickness was obtained. Finally the molded product was dried at 70° C. for 12 hours. Then the molded product was washed in flowing water for one week and was dried, giving a urethral catheter.

The obtained urethral catheter was immersed in an aqueous solution of silver perchlorate adjusted to a concentration of 0.005% and was shaken at 30° C. for 24 hours. Thereafter the urethral catheter was washed with water and was dried at 70° C., giving an antibacterial urethral catheter. The anibacterial property was evaluated in the same manner as in Example 1. The results are shown in Table 1.

Example 3

A natural rubber latex specimen was prepared by adding 0.5 part of zinc salt of 2-mercaptobenzothiazole, 1.5 parts of sulfur colloid, 1.0 part of activated zinc and 0.1 part of disodium N-lauroyl-L-glutamate to 100 parts of a natural rubber latex having a solids concentration of 60%. The natural rubber latex specimen had a pH of 10.0. A dipping mold for molding a urethral catheter was immersed in the obtained natural rubber latex specimen and was withdrawn from the latex specimen. The molded product thus obtained was dried at 80° C. for 10 minutes. This operation was repeated until a molded product of 1.6 mm thickness was obtained. Finally the molded product was dried at 70° C. for 12 hours. Then the molded product was washed in flowing water for one week and was dried, giving a urethral catheter.

The obtained urethral catheter was immersed in an aqueous solution of silver acetate adjusted to a concentration of 0.01% and was shaken at 35° C. for 24 hours. Thereafter the urethral catheter was washed with water and was dried at 70° C., giving an antibacterial urethral catheter. The anibacterial property was evaluated in the same manner as in Example 1. The results are shown in Table 1.

Example 4

A synthetic rubber latex specimen was prepared by adding 0.5 part of zinc salt of 2-mercaptobenzothiazole, 1.5 parts of sulfur colloid, 1.0 part of activated zinc and 0.1 part of disodium N-lauroyl-L-glutamate to 100 parts of an anionic styrene-butadiene copolymer latex having a solids concentration of 50%. The synthetic rubber latex specimen had a pH of 10.0. A dipping mold for molding a urethral catheter was immersed in the obtained synthetic rubber latex specimen and was withdrawn from the latex specimen. The molded product thus obtained was dried at 80° C. for 10 minutes. This operation was repeated until a molded product of 1.6 mm thickness was obtained. Finally the molded product was dried at 70° C. for 12 hours. Then the molded product was washed in flowing water for one week and was dried, giving a urethral catheter.

The obtained urethral catheter was immersed in an aqueous solution of silver acetate adjusted to a concentration of 0.01% and was shaken at 35° C. for 24 hours. Thereafter the urethral catheter was washed with water and was dried at 70° C., giving an antibacterial urethral catheter. The anibacterial property was evaluated in the same manner as in Example 1. The results are shown in Table 1.

Example 5

A synthetic rubber latex specimen was prepared by adding 0.3 part of zinc dimethyldithiocarbamate, 1.5 parts of sulfur colloid, 3.0 parts of activated zinc and 0.5 part of sodium dimethyl-5-sulfoisophthalate to 100 parts of an anionic chloroprene latex having a solids concentration of 50%. The synthetic rubber latex specimen had a pH of 10.5. A dipping mold for molding a urethral catheter was immersed in the obtained synthetic rubber latex specimen and was withdrawn from the latex specimen. The molded product thus obtained was dried at 80° C. for 10 minutes. This operation was repeated until a molded product of 1.6 mm thickness was obtained. Finally the molded product was dried at 70° C. for 12 hours. Then the molded product was washed in flowing water for one week and was dried, giving a urethral catheter.

The obtained urethral catheter was immersed in an aqueous solution of silver acetate adjusted to a concentration of 0.01% and was shaken at 35° C. for 24 hours. Thereafter the urethral catheter was washed with water and was dried at 70° C., giving an antibacterial urethral catheter. The anibacterial property was evaluated in the same manner as in Example 1. The results are shown in Table 1.

Example 6

Mixed together were 100 parts of methylvinyl polysiloxane, 20 parts of silicic anhydride, 0.5 part of benzoyl peroxide, and 0.5 part of sodium dimethyl-5-sulfoisophthalate. The mixture was kneaded well and was extruded. The obtained extrudate was heated at 200° C. for 2 minutes and was post-vulcanized at 130° C. for 7 days, giving a urethral catheter.

The obtained urethral catheter was immersed in an aqueous solution of silver nitrate adjusted to a concentration of 0.05% and was shaken at 50° C. for 24 hours. Thereafter the urethral catheter was washed with water and was dried at 70° C., giving an antibacterial urethral catheter. The anibacterial property was evaluated in the same manner as in Example 1. The results are shown in Table 1.

Example 7

Mixed together were 100 parts of methylvinl polysiloxane, 20 parts of silicic anhydride, 0.5 part of benzoyl peroxide, and 0.01 part of disodium N-lauroyl-L-glutamate. The mixture was kneaded well and was extruded. The obtained extrudate was heated at 200° C. for 2 minutes and was post-vulcanized at 130° C. for 7 days, giving a urethral catheter.

The obtained urethral catheter was immersed in an aqueous solution of silver nitrate adjusted to a concentration of 0.0001% and was shaken at 50° C. for 3 days. Thereafter the urethral catheter was washed with water and was dried at 70° C., giving an antibacterial urethral catheter. The anibacterial property was evaluated in the same manner as in Example 1. The results are shown in Table 1.

Example 8

A natural rubber latex specimen was prepared by adding 0.3 part of zinc dimethyldithiocarbamate, 1.5 parts of sulfur colloid and 3.0 parts of activated zinc to 100 parts of a natural rubber latex having a solids concentration of 60%. The natural rubber latex specimen had a pH of 10.5.

A dipping mold for molding a urethral catheter was immersed in the obtained natural rubber latex specimen and was withdrawn from the latex specimen. The molded product thus obtained was dried at 80° C. for 10 minutes. This operation was repeated until a molded product of 1.6 mm thickness was obtained. Finally the molded product was dried at 70° C. for 12 hours. Then the molded product was leached at 50° C. for 10 hours, giving a urethral catheter. The obtained urethral catheter was immersed in an aqueous solution of sodium stearate adjusted to a concentration of 0.1% at 80° C. for 20 hours. After the urethral catheter was washed with water, it was immersed in an aqueous solution of silver acetate adjusted to a concentration of 0.05% and was shaken at 50° C. for 12 hours. The catheter was washed with water again and was dried at 60° C., giving an antibacterial urethral catheter. The anibacterial property was evaluated in the same manner as in Example 1. The results are shown in Table 1.

Example 9

A natural rubber latex specimen was prepared by adding 0.3 part of zinc dimethyldithiocarbamate, 1.5 parts of sulfur colloid and 3.0 parts of activated zinc to 100 parts of a deproteinized natural rubber latex having a solids concentration of 50%. The natural rubber latex specimen had a pH of 10.5.

A dipping mold for molding a urethral catheter was immersed in the obtained natural rubber latex specimen and was withdrawn from the latex specimen. The molded product thus obtained was dried at 80° C. for 10 minutes. This operation was repeated until a molded product of 1.6 mm thickness was obtained. Finally the molded product was dried at 70° C. for 12 hours, giving a urethral catheter. The obtained urethral catheter was immersed in an aqueous solution of disodium N-stearoyl-L-glutamate adjusted to a concentration of 1.0% at 50° C. for 24 hours. After the urethral catheter was washed with water, it was immersed in an aqueous solution of silver nitrate adjusted to a concentration of 0.01% and was shaken at 30° C. for 24 hours. The catheter was washed with water again and was dried at 60° C., giving an antibacterial urethral catheter. The anibacterial property was evaluated in the same manner as in Example 1. The results are shown in Table 1.

Example 10

Mixed together were 100 parts of methylvinl polysiloxane, 20 parts of silicic anhydride, and 0.5 part of benzoyl peroxide. The mixture was kneaded well and was extruded. The obtained extrudate was heated at 200° C. for 2 minutes and was post-vulcanized at 130° C. for 7 days, giving a urethral catheter.

The obtained urethral catheter was immersed in an aqueous solution of sodium laurylbenzene sulfonate adjusted to a concentration of 0.01% at 90° C. for 12 hours. Thereafter the urethral catheter was washed with water and was immersed in an aqueous solution of silver perchlorate adjusted to a concentration of 0.1% and was shaken at 40° C. for 18 hours. The urethral catheter was washed with water again and was dried at 60° C., giving an antibacterial urethral catheter. The anibacterial property was evaluated in the same manner as in Example 1. The results are shown in Table 1.

Example 11

A synthetic rubber latex specimen was prepared by adding 0.5 part of zinc salt of 2-mercaptobenzothiazole, 1.5 parts of sulfur colloid and 1.0 part of activated zinc to 100 parts of an anionic styrene-butadiene copolymer latex having a solids concentration of 50%. The synthetic rubber latex specimen had a pH of 10.5. A dipping mold for molding gloves was immersed in the obtained synthetic rubber latex specimen and was withdrawn from the latex specimen. The molded product thus obtained was thermally vulcanized at 70° C. for 12 hours, giving gloves.

The obtained gloves were immersed in an aqueous solution of taurine adjusted to a concentration of 5% at 30° C. for 3 hours. After the gloves were washed with water, they were immersed in an aqueous solution of silver nitrate adjusted to a concentration of 0.1%, and were shaken at 80° C. for 1 hour. The gloves were washed with water again and were dried at 50° C., giving antibacterial gloves.

The antibacterial gloves were partly cut to a square shape, 5 cm×5 cm. The anibacterial property was evaluated in the same manner as in Example 1. The results are shown in Table 1.

Comparative Example 1

A natural rubber latex specimen was prepared by adding 0.3 part of zinc dimethyldithiocarbamate, 1.5 parts of sulfur colloid and 3.0 parts of activated zinc to 100 parts of a natural rubber latex having a solids concentration of 60%. The natural rubber latex specimen had a pH of 10.0.

A dipping mold for molding a urethral catheter was immersed in the obtained natural rubber latex specimen and was withdrawn from the latex specimen. The molded product thus obtained was dried at 80° C. for 10 minutes. This operation was repeated until a molded product of 1.6 mm thickness was obtained. Finally the molded product was dried at 70° C. for 12 hours. Then the molded product was washed in flowing water for one week and was dried, giving a urethral catheter. The anibacterial property was evaluated in the same manner as in Example 1. The results are shown in Table 1.

Comparative Example 2

A natural rubber latex specimen was prepared by adding 0.3 part of zinc dimethyldithiocarbamate, 1.5 parts of sulfur colloid, 3.0 parts of activated zinc and 0.5 part of sodium dimethyl-5-sulfoisophthalate to 100 parts of a natural rubber latex having a solids concentration of 60%. The natural rubber latex specimen had a pH of 10.0. A dipping mold for molding a urethral catheter was immersed in the obtained natural rubber latex specimen and was withdrawn from the latex specimen. The molded product thus obtained was dried at 80° C. for 10 minutes. This operation was repeated until a molded product of 1.6 mm thickness was obtained. Finally the molded product was dried at 70° C. for 12 hours. Then the molded product was washed in flowing water for one week and dried, giving a urethral catheter. The anibacterial property was evaluated in the same manner as in Example 1. The results are shown in Table 1.

Comparative Example 3

A natural rubber latex specimen was prepared by adding 0.3 part of zinc dimethyldithiocarbamate, 1.5 parts of sulfur colloid and 3.0 parts of activated zinc to 100 parts of a natural rubber latex having a solids concentration of 60%. The natural rubber latex specimen had a pH of 10.0. A dipping mold for molding a urethral catheter was immersed in the obtained natural rubber latex specimen and was withdrawn from the latex specimen. The molded product thus obtained was dried at 80° C. for 10 minutes. This operation was repeated until a molded product of 1.6 mm thickness was obtained. Finally the molded product was dried at 70° C. for 12 hours. Then the molded product was washed in flowing water for one week and was dried, giving a urethral catheter.

The urethral catheter was immersed in an aqueous solution of silver nitrate adjusted to a concentration of 0.01% and was shaken at 30° C. for 12 hours. The catheter was washed with water again and was dried at 70° C. The anibacterial property was evaluated in the same manner as in Example 1. The results are shown in Table 1.

Comparative Example 4

A natural rubber latex specimen was prepared by adding 0.3 part of zinc dimethyldithiocarbamate, 1.5 parts of sulfur colloid and 3.0 parts of activated zinc to 100 parts of a natural rubber latex having a solids concentration of 60%. The natural rubber latex specimen had a pH of 10.5.

A dipping mold for molding gloves was immersed in the obtained natural rubber latex specimen and was withdrawn from the latex specimen. The molded product thus obtained was thermally vulcanized at 70° C. for 12 hours. Thereafter the molded product was leached at 50° C. for 10 hours, giving gloves. The gloves were immersed in an aqueous solution of silver acetate adjusted to a concentration of 0.005% and were shaken at 30° C. for 3 hours. The gloves were washed with water again and were dried at 50° C. The anibacterial property was evaluated in the same manner as in Example 1. The results are shown in Table 1.

Comparative Example 5

A natural rubber latex specimen was prepared by adding 0.3 part of zinc dimethyldithiocarbamate, 1.5 parts of sulfur colloid and 3.0 parts of activated zinc to 100 parts of a natural rubber latex having a solids concentration of 60%. The natural rubber latex specimen had a pH of 10.5.

A dipping mold for molding gloves was immersed in the obtained natural rubber latex specimen and was withdrawn from the latex specimen. The molded product thus obtained was thermally vulcanized at 70° C. for 12 hours. Thereafter the molded product was leached at 50° C. for 10 hours, giving gloves. The gloves were immersed in an aqueous solution of taurine adjusted to a concentration of 1.0% and were shaken at 30° C. for 2 hours. The gloves were washed with water again and were dried at 50° C. The anibacterial property was evaluated in the same manner as in Example 1. The results are shown in Table 1.

TABLE 1

| | Pseudomonas aeruginosa | Escherichia coli | Staphylococcus aureus |
|---|---|---|---|
| Example 1 | Less than 200 | Less than 200 | Less than 200 |
| Example 2 | $8.96 \times 10^2$ | $6.35 \times 10^2$ | Less than 200 |
| Example 3 | Less than 200 | Less than 200 | Less than 200 |
| Example 4 | Less than 200 | Less than 200 | Less than 200 |
| Example 5 | Less than 200 | Less than 200 | Less than 200 |
| Example 6 | Less than 200 | Less than 200 | Less than 200 |
| Example 7 | $4.74 \times 10^2$ | $4.09 \times 10^2$ | $2.59 \times 10^2$ |
| Example 8 | Less than 200 | Less than 200 | Less than 200 |
| Example 9 | Less than 200 | Less than 200 | Less than 200 |
| Example 10 | $2.01 \times 10^3$ | $4.90 \times 10^2$ | Less than 200 |
| Example 11 | $5.93 \times 10^3$ | $2.24 \times 10^2$ | Less than 200 |
| Comp. Ex. 1 | $3.29 \times 10^7$ | $4.10 \times 10^7$ | $1.64 \times 10^7$ |
| Comp. Ex. 2 | $6.55 \times 10^7$ | $2.34 \times 10^7$ | $2.85 \times 10^7$ |
| Comp. Ex. 3 | $4.12 \times 10^6$ | $2.58 \times 10^6$ | $7.51 \times 10^6$ |
| Comp. Ex. 4 | $2.81 \times 10^6$ | $1.35 \times 10^6$ | $5.10 \times 10^6$ |
| Comp. Ex. 5 | $7.68 \times 10^7$ | $1.62 \times 10^7$ | $4.60 \times 10^7$ |

Unit: cell/ml

What is claimed is:

1. An antibacterial polymeric molded product containing at least one anionic compound capable of combining by ionic bond, with a cationic component of a water-soluble antibacterial agent, which is selected from the group consisting of sodium dimethyl-5-sulfoisophthalate, taurine, disodium N-lauroyl-L-glutamate, disodium N-stearoyl-L-glutamate, sodium stearate, sodium laurylbenzene sulfonate and sodium laurate, wherein the cationic component is combined with the anionic compound by ionic bond at least at the surface of the molded product, said antibacterial polymeric molded product prepared by a process comprising molding a polymeric compound containing the anionic compound, and contacting the molded product with an aqueous solution containing the water-soluble antibacterial agent.

2. An antibacterial polymeric molded product containing at least one anionic compound capable of combining by ionic bond, with a cationic component of water-soluble antibacterial agent, which is selected from the group consisting of sodium dimethyl-5-sulfoisophthalate, taurine, disodium N-lauroyl-L-glutamate, disodium N-stearoyl-L-glutamate, sodium stearate, sodium laurylbenzene sulfonate and sodium laurate, wherein the cationic component is combined with the anionic compound by ionic bond at least at the surface of the molded product, said antibacterial polymeric molded product prepared by a process comprising molding a polymeric compound, contacting the molded product with an aqueous solution containing the anionic compound, and contacting the molded product with an aqueous solution containing the water-soluble antibacterial agent.

3. The molded product according to claim 1 or 2 which is one formed from natural rubber, synthetic rubber, silicone rubber or a synthetic polymeric compound.

4. The molded product according to claim 1 or 2, wherein the water-soluble antibacterial agent is at least one member selected from the group consisting of silver compounds, quaternary ammonium salts and quaternary phosphonium salts.

5. The molded product according to claim 1 or 2 which is an antibacterial urethral catheter.

6. The molded product according to claim 1 or 2 which is an antibacterial glove.

7. A process for preparing the molded product of claim 1, the process comprising the steps of molding a polymeric compound containing at least one anionic compound selected from the group consisting of sodium dimethyl-5-sulfoisophthalate, taurine, disodium N-lauroyl-L-glutamate, disodium N-stearoyl-L-glutamate, sodium stearate, sodium laurylbenzene sulfonate and sodium laurate; and contacting the molded product with an aqueous solution containing a water-soluble antibacterial agent.

8. A process for preparing the molded product of claim 2, the process comprising the steps of molding a polymeric compound; contacting the molded product with an aqueous solution containing at least one anionic compound selected from the group consisting of sodium dimethyl-5-sulfoisophthalate, taurine, disodium N-lauroyl-L-glutamate, disodium N-stearoyl-L-glutamate, sodium stearate, sodium laurylbenzene sulfonate and sodium laurate; and contacting the molded product with an aqueous solution containing a water-soluble antibacterial agent.

* * * * *